(12) United States Patent
Crossman

(10) Patent No.: US 7,691,081 B2
(45) Date of Patent: Apr. 6, 2010

(54) EXPANDABLE COMPONENT GUIDE WIRE SYSTEM AND RELATED METHOD OF USING THE SAME

(76) Inventor: Arthur W. Crossman, 1723 N. Halifax Ave., Daytona Beach, FL (US) 32118

( * ) Notice: Subject to any disclaimer, the term of this patent is extended or adjusted under 35 U.S.C. 154(b) by 170 days.

(21) Appl. No.: 11/592,560

(22) Filed: Nov. 3, 2006

(65) Prior Publication Data

US 2007/0112369 A1 May 17, 2007

Related U.S. Application Data

(60) Provisional application No. 60/733,489, filed on Nov. 5, 2005, provisional application No. 60/808,837, filed on May 26, 2006.

(51) Int. Cl.
*A61M 29/00* (2006.01)
(52) U.S. Cl. .................................. 604/99.04
(58) Field of Classification Search ............ 601/101.01, 601/101.04, 103.01; 604/101.01, 101.04, 604/103.01, 96.01, 101.02, 101.05, 102.02, 604/102.03, 103.04; 606/194
See application file for complete search history.

(56) References Cited

U.S. PATENT DOCUMENTS

| | | |
|---|---|---|
| 4,273,128 A | 6/1981 | Lary |
| 4,543,087 A | 9/1985 | Sommercorn |
| 4,738,666 A | 4/1988 | Fuqua |
| 5,002,532 A | 3/1991 | Gaiser |
| 5,021,043 A | 6/1991 | Becker |
| 5,084,010 A | 1/1992 | Plaia |
| 5,169,386 A | 12/1992 | Becker |
| 5,234,416 A | 8/1993 | Macaulay |
| 5,395,333 A | 3/1995 | Brill |
| 5,505,730 A | 4/1996 | Edwards |
| 5,617,854 A | 4/1997 | Munsif |
| 5,687,723 A | 11/1997 | Avitall |
| 5,695,457 A | 12/1997 | St. Goar |
| 5,775,327 A | 7/1998 | Randolph |
| 5,807,318 A | 9/1998 | St. Goar |

(Continued)

FOREIGN PATENT DOCUMENTS

WO WO 2006/044670 4/2006

(Continued)

*Primary Examiner*—Nicholas D Lucchesi
*Assistant Examiner*—Christopher D Koharski
(74) *Attorney, Agent, or Firm*—Robert J. Decker

(57) ABSTRACT

A catheter device and related method for diagnostic vascular treatment and/or therapeutic vascular treatment of a subject's vasculature having a lesion. The device including: a guide catheter comprising a shaft having a proximal portion and a distal portion; a guide wire disposed in the guide catheter shaft having a proximal portion and a distal portion, the guide wire transfers beyond the lesion during at least a portion of the vascular treatment and/or therapeutic vascular treatment; and one or more expandable component disposed at the distal portion of the guide wire. The expandable component(s) may be positioned distally beyond the lesion during at least a portion of the vascular treatment and/or therapeutic vascular treatment. The expandable component(s) being used to: anchor said guide wire to mitigate and/or prevent loss of guide wire position during at least a portion of the vascular treatment and/or therapeutic vascular treatment; and avoid and/or mitigate trauma to the vasculature during at least a portion of the vascular treatment and/or therapeutic vascular treatment.

20 Claims, 2 Drawing Sheets

U.S. PATENT DOCUMENTS

| | | | |
|---|---|---|---|
| 5,833,650 | A | 11/1998 | Imran |
| 5,868,703 | A | 2/1999 | Bertolero |
| 6,013,072 | A | 1/2000 | Winston |
| 6,086,581 | A | 7/2000 | Reynolds |
| 6,126,649 | A | 10/2000 | VanTassel |
| 6,270,480 | B1 | 8/2001 | Dorr |
| 6,290,697 | B1 | 9/2001 | Tu et al. |
| 6,383,151 | B1 | 5/2002 | Diederich |
| 6,447,462 | B1 | 9/2002 | Wallace |
| 6,491,710 | B2 | 12/2002 | Satake |
| 6,503,247 | B2 | 1/2003 | Swartz |
| 6,512,957 | B1 | 1/2003 | Witte |
| 6,629,987 | B1 | 10/2003 | Gambale |
| 6,632,223 | B1 | 10/2003 | Keane |
| 6,638,247 | B1 | 10/2003 | Selmon |
| 6,663,621 | B1 | 12/2003 | Winston |
| 6,702,811 | B2 | 3/2004 | Stewart |
| 6,723,082 | B1 | 4/2004 | Payne |
| 6,730,063 | B2 | 5/2004 | Delaney |
| 6,746,462 | B1 | 6/2004 | Selmon |
| 6,758,847 | B2 | 7/2004 | Maquire |
| 6,770,059 | B1 | 8/2004 | Spinks |
| 6,773,447 | B2 | 8/2004 | Laguna |
| 6,808,524 | B2 | 10/2004 | Lopath |
| 6,811,544 | B2 | 11/2004 | Schaer |
| 6,926,714 | B1 | 8/2005 | Sra |
| 6,936,056 | B2 | 8/2005 | Nash |
| 2001/0023334 | A1 | 9/2001 | St. Goar |
| 2003/0088211 | A1* | 5/2003 | Anderson et al. ...... 604/103.01 |
| 2003/0130610 | A1 | 7/2003 | Mager |
| 2003/0163156 | A1* | 8/2003 | Hebert et al. ................ 606/194 |
| 2003/0195510 | A1 | 10/2003 | Schaer |
| 2004/0158141 | A1 | 8/2004 | Scheib |
| 2004/0162519 | A1 | 8/2004 | Helkowski |
| 2005/0165391 | A1 | 7/2005 | Maguire |
| 2008/0249420 | A1 | 10/2008 | Crossman |

FOREIGN PATENT DOCUMENTS

| | | |
|---|---|---|
| WO | WO 2007/053777 | 5/2007 |
| WO | WO 2007/076045 | 7/2007 |

* cited by examiner

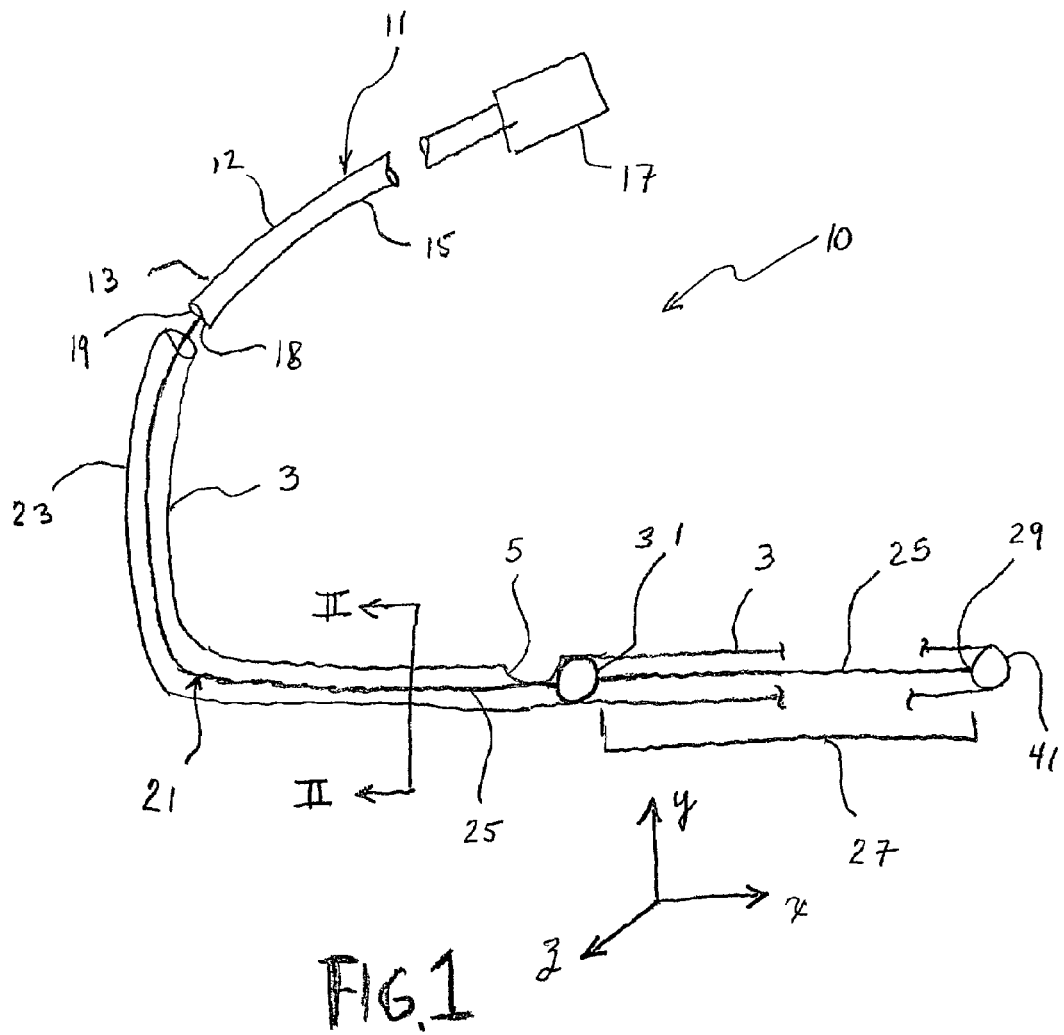
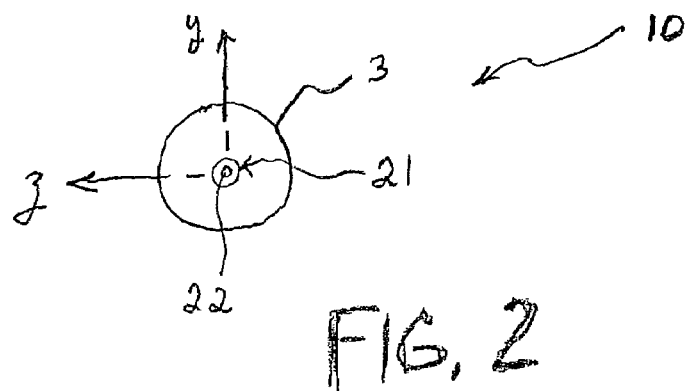

EXPANDABLE COMPONENT GUIDE WIRE SYSTEM AND RELATED METHOD OF USING THE SAME

CROSS-REFERENCES TO RELATED APPLICATION

The present application claims priority under 35 U.S.C. Section 119(e) of the earlier filing dates of U.S. Provisional Patent Application Ser. No. 60/733,489, filed on Nov. 5, 2005, entitled "Balloon Guide Wire System and Related Method of Using the Same" and U.S. Provisional Patent Application Ser. No. 60/808,837, filed on May 26, 2006, entitled "Expandable Component Guide Wire System and Related Method of Using the Same," the disclosures of which are hereby incorporated herein in their entirety.

BACKGROUND OF THE INVENTION

Diagnostic vascular catheterization is a classification of invasive procedures in which a catheter and related are passed into a peripheral vein or artery, through the blood vessels, and into the heart or other vasculature. These procedures permit the study of the heart chambers and the arteries supplying the heart or other vasculatures of the body to diagnose illness or disease. Some examples of diagnostic vascular catheterization are, but not limited thereto, are coronary and peripheral vascular (e.g., renal artery, iliofemoral, aortic, cerebrovascular) angiography (or coronary arteriogaphy and angiography).

Therapeutic vascular catheterization (i.e., interventional catheterization) is a classification of invasive procedures in which a catheter and related are passed into a peripheral vein or artery, through the blood vessels, and into the heart or other vasculature. These procedures are intended primarily for the treatment of cardiac illness and disease as well as other vasculature illnesses and diseases. Often the goals of therapeutic vascular catheterization (interventional catheterization) have some similarities to diagnostic catheterization, except the goal is placement of the catheter to treat an underlying condition. Some examples of therapeutic cardiac catheterization are, but not limited thereto, percutaneous transluminal angioplasty (PTA) (alternatively, percutaneous transluminal coronary angioplasty (PTCA)), percutaneous coronary intervention (PCI), and percutaneous transluminal interventions (PTI). Interventional catherization to include, for example, all transluminal mechanisms of vascular lumen enlargement.

Some drawbacks that are associated with the various diagnostic and therapeutic vasculature catheterizations are, but not limited thereto, the unnecessary complications that can occur and restricted operations related to advancing or moving a guide wire. For example, but not limited thereto, when a guide is at the ostium of the coronary artery a 0.014 inch guide wire or any applicable sized guide wire is passed into the artery beyond the lesion or stenosis with the wire tip positioned distal to the lesion or stenosis. The physician then slides a dilatation device, e.g., stent or expandable component, over the guide wire (via a monorail catheter system or an over-the-wire catheter system) to the position of the lesion or stenosis. If the lesion or stenosis is too tight (i.e., smaller diameter than the undeployed stent) the stent cannot be delivered without some degree of leverage. The leverage can be achieved through the use of various guide manipulations and different types of guides. Despite adequate leverage (or extra support from the guide) by pushing the stent or dilation devices (such as expandable component, rotor bladder, stents, atherectomy devices, lasers, thrombectomy devices, etc.) the guide may be pushed backward thus passively pulling the guide wire with it. Further yet, sometimes when the guide is pushed backwards, due to the stored torque, potential energy, the guide can be dislodged more significantly over a greater distance thereby pulling the entire wire not only proximal to the lesion, but potentially completely out of the artery. While the leverage may be achieved by manipulating the guide this may lead to vessel trauma, cardiac trauma, etc. Further, the leveraging manipulation may also be unsuccessful when a device (such as a expandable component or stent) is transmitted on the guide wire that pushes the device against a lesion or stenosis, which in turn imposes a reactive force onto the guide catheter. The reactive force exerted on the guide causes the guide to move backwards with the wire also typically being pulled backwards with the guide, thereby passively pulling the guide wire across and proximally to the lesion or stenosis. If the guide wire moves backward across the lesion or stenosis then potentially the lesion may not be able to be re-crossed again thereby eliminating possible treatment of the lesion or stenosis. Also, when the physician tries to advance the device across a resistant lesion in a back and forth movement the guide wire will also go back and forth in a to and fro type motion and each time the wire tip goes forward it may injure the vessel. It should be appreciated that the to and fro motion of the guide wire leads to the wire tip potentially causing vessel injury with each forward advancement because it can catch onto a plaque, for example, and cause dissection leading to vessel occlusion, plaque disruption leading to thrombosis and vessel occlusion and vessel perforation all of which have a high risk of leading to death, tissue infarction, stroke, hemorrhage and circulatory collapse as well as emergency surgery. It should be appreciated that even if the lesion or stenosis has been pre-dilated the aforementioned risks, such as dissection, are more likely to occur because when re-crossing the lesion or stenosis the guide wire tip may enter a dissection plane.

One should appreciate that in the event that a guide wire is successfully transmitted across a lesion but is then undesirably/unintentionally withdrawn then the guide wire will need to be repositioned forward across the lesion. The second re-crossing (or any subsequent re-crossing thereafter) of the lesion may be significantly more difficult and/or risky compared to the first (or a previous) forward placement.

Further, if the lesion has been pre-dilated with a expandable component or pre-treated with a rotor bladder, atherectomy devices, lasers, thrombectomy devices, etc., dissection planes commonly occur. Therefore, when the physician tries to re-cross the lesion with a 0.014 inch diameter guide wire (or any applicable size guide wire) then the guide wire can easily track between layers of the artery causing a dissection or propagating a previous dissection and thus occluding the artery, causing a myocardial infarction and all of its sequelae. A pre-dilated lesion typically provides a dissection inherently.

There is therefore a need in the art for a more effective and safer method of wire positioning and prevention of wire tip vessel trauma while practicing diagnostic and therapeutic vasculature catheterization. The various aspects of the embodiments of the present invention overcome and/or mitigate the aforementioned problems.

BRIEF SUMMARY OF INVENTION

In an aspect of an embodiment of the present invention expandable component anchored guide wire and related method, the embodiment includes placing a small inflatable expandable component where the expandable component will be distal from the lesion or stenosis. When the guide wire tip is positioned across the lesion or stenosis then an anchor expandable component may be gently inflated just distal from the lesion or stenosis. This will now anchor the guide wire in position so it will be less likely to be pulled backward across the lesion or stenosis. For instance, when a physician pushes a stent over the guide wire forward against a resistant stenotic lesion the guide wire will not back out, even if the guide catheter does, or will be less likely to back out compared with conventional practices.

In an aspect of an embodiment the anchor expandable component is inflated just distal to the lesion or stenosis wherein the lesion or stenosis itself would further act as an anchoring mechanism. Because the anchor expandable component may be small and is inflated just beyond the lesion or stenosis the potentially injured endothelium could be covered by a stent. Specifically the expandable component would be very short, e.g., less than about 4 mm (or sized/contoured as desired or required), so as to minimize endothelial contact surface area.

In an aspect of an embodiment, a tip expandable component may be provided at or proximal to the wire distal tip and will act as, among other things, a trauma mitigating or trauma avoidance device or mechanism. For instance, when the guide wire distal tip is positioned distal to the lesion then the tip expandable component may be gently inflated so as not to rupture or perforate or damage the vessel. This will now allow the guide wire distal tip to be less prone to injuring the vessel as it is moved in a forward direction, for example.

An aspect of an embodiment of the present invention provides a catheter device for diagnostic vascular treatment and/or therapeutic vascular treatment of a subject's vasculature having a lesion. The device comprising: a guide catheter comprising a shaft having a proximal portion and a distal portion; a guide wire disposed in the guide catheter shaft having a proximal portion and a distal portion, wherein the guide wire being adapted to transfer beyond the lesion during at least a portion of the vascular treatment and/or therapeutic vascular treatment; and a first expandable component disposed on the guide wire to be positioned distally beyond the lesion during at least a portion of the vascular treatment and/or therapeutic vascular treatment. The first expandable component being adapted to anchor the guide wire to mitigate and/or prevent loss of guide wire position during at least a portion of the vascular treatment and/or therapeutic vascular treatment. An aspect of an embodiment of the present invention device may further comprise a second expandable component disposed at the distal portion of the guide wire. The second expandable component adapted to prevent and/or mitigate trauma to the vasculature during at least a portion of the vascular treatment and/or therapeutic vascular treatment.

An aspect of an embodiment of the present invention provides a catheter device for diagnostic vascular treatment and/or therapeutic vascular treatment of a subject's vasculature having a lesion. The device comprising: a guide catheter comprising a shaft having a proximal portion and a distal portion; a guide wire disposed in the guide catheter shaft having a proximal portion and a distal portion, wherein the guide wire adapted to transfer beyond the lesion during at least a portion of the vascular treatment and/or therapeutic vascular treatment; and an expandable component. The expandable component disposed at the distal portion of the guide wire, wherein the expandable component to be positioned distally beyond the lesion during at least a portion of the vascular treatment and/or therapeutic vascular treatment. The expandable component being adapted to anchor the guide wire to mitigate and/or prevent loss of guide wire position during at least a portion of the vascular treatment and/or therapeutic vascular treatment and the expandable component adapted to avoid and/or mitigate trauma to the vasculature during at least a portion of the vascular treatment and/or therapeutic vascular treatment.

An aspect of an embodiment of the present invention provides a catheter method for diagnostic vascular treatment and/or therapeutic vascular treatment of a subject's vasculature having a lesion. The method comprising: providing a guide catheter comprising a shaft having a proximal portion and a distal portion; providing a guide wire disposed in the guide catheter shaft having a proximal portion and a distal portion; and transferring the guide wire beyond the lesion during at least a portion of the vascular treatment and/or therapeutic vascular treatment. The method further comprises providing a first expandable component disposed on the guide wire and positioning the first expandable component distally beyond the lesion during at least a portion of the vascular treatment and/or therapeutic vascular treatment and anchoring the guide wire using the first expandable component to mitigate and/or prevent loss of guide wire position during at least a portion of the vascular treatment and/or therapeutic vascular treatment to anchor. An aspect of an embodiment of the present invention further comprises providing a second expandable component disposed at the distal portion of the guide wire, and preventing and/or mitigating trauma to the vasculature using the second expandable component during at least a portion of the vascular treatment and/or therapeutic vascular treatment.

An aspect of an embodiment of the present invention provides a catheter method for diagnostic vascular treatment and/or therapeutic vascular treatment of a subject's vasculature having a lesion. The method comprising: providing a guide catheter comprising a shaft having a proximal portion and a distal portion; providing a guide wire disposed in the guide catheter shaft having a proximal portion and a distal portion; transferring the guide wire beyond the lesion during at least a portion of the vascular treatment and/or therapeutic vascular treatment; and providing an expandable component disposed at the distal portion of the guide wire. The method comprises positioning the expandable component distally beyond the lesion during at least a portion of the vascular treatment and/or therapeutic vascular treatment and anchoring the guide wire using the expandable component to mitigate and/or prevent loss of guide wire position during at least a portion of the vascular treatment and/or therapeutic vascular treatment. The method comprises providing the expandable component to avoid and/or mitigate trauma to the vasculature during at least a portion of the vascular treatment and/or therapeutic vascular treatment.

These and other aspects of the disclosed technology and systems, along with their advantages and features, will be made more apparent from the description and drawings that follow.

BRIEF SUMMARY OF THE DRAWINGS

The foregoing and other objects, features and advantages of the present invention, as well as the invention itself, will be more fully understood from the following description of preferred embodiments, when read together with the accompanying drawings, in which:

FIG. 1 illustrates a schematic elevation view of an embodiment of the present invention catheter device with a guide wire having a expandable component anchor and/or expandable component tip.

FIG. 2 illustrates a cross-section view II-II as shown in FIG. 1 of the guide wire expandable component(s) system of the catheter device.

DETAILED DESCRIPTION OF THE INVENTION

Figure 3:
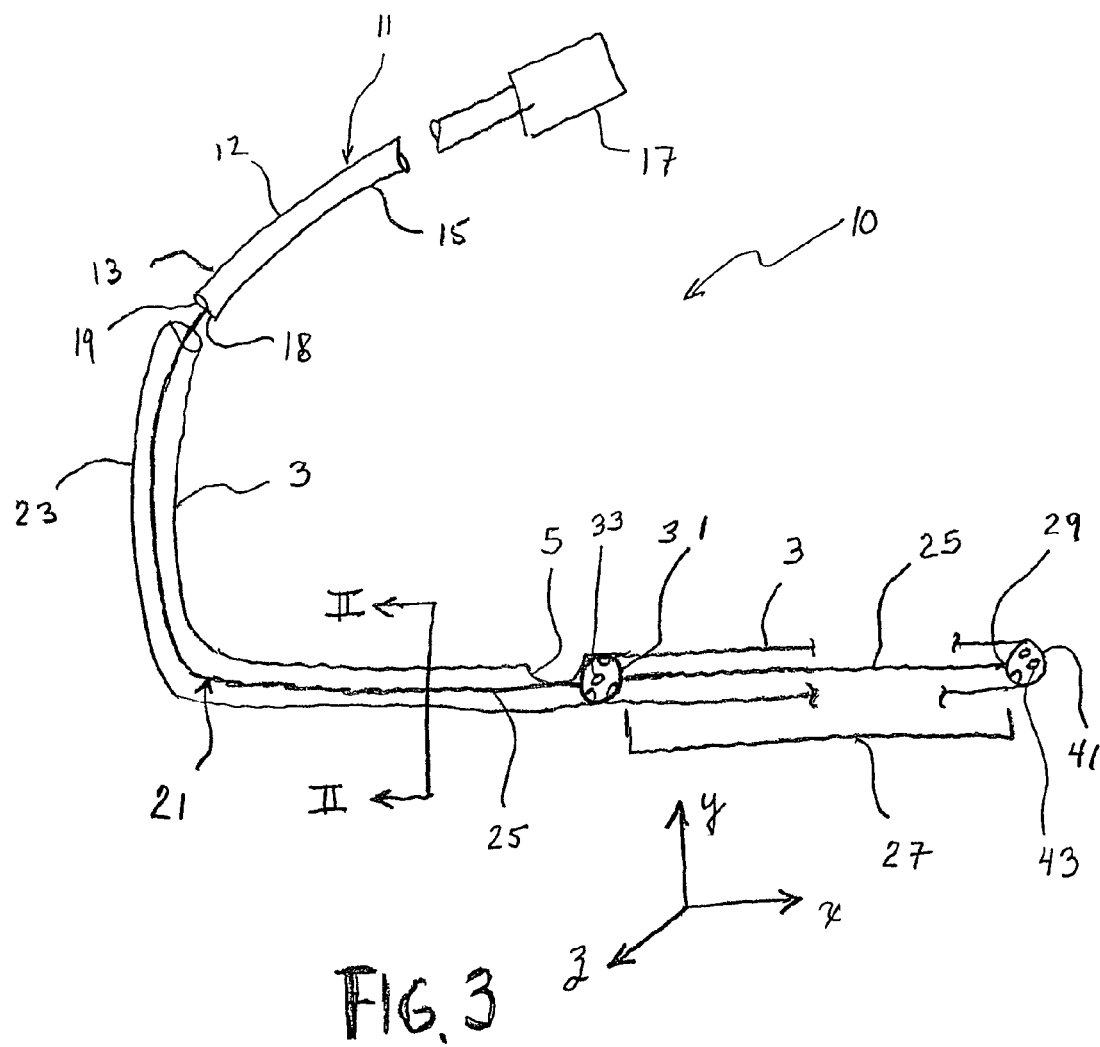
FIG. 3 illustrates a schematic elevation view of an embodiment of the present invention catheter device having apertures disposed on its expandable component anchor and/or expandable component tip.

Turning to FIG. 1, FIG. 1 illustrates a schematic elevation view of an embodiment of the present invention catheter device 10 including a catheter guide 11 having a catheter shaft 12 with a proximal portion 13 and distal portion 15 of the guide, interface device 17 and an orifice 18 defined by a guide catheter lumen 19. The catheter device 10 further includes a guide wire 21 that is inserted into a vasculature 3 (e.g., right coronary artery), such as an artery, vein or the like, as the catheter guide 11 sits at the ostium of the vasculature 3, at a proximal portion of the vasculature 3, or at a location of the vasculature as required or desired. The guide wire 21 includes a proximal portion 23 and distal portion 25 of the guide wire 21, and a distal tip 29, and an anchor expandable component 31 (balloon or inflatable compartment) that may be disposed at or proximal to the beginning of the distal extension 27 of the guide wire 21, as well as any portion of the distal extension 27. The distal extension 27 may be any desired or required dimension such as about 100 com or more, about 10 cm or more, about 5 cm or more, 1 cm or more, less than about 1 cm, or less than 1 mm. The distance of the distal extension 27 may be any variable length according to the desired or required procedure/treatment on the subject or patient. In an embodiment, the distal extension 27 may be equal to zero thereby defining the location of the expandable component at or proximal to the distal tip 29.

In an embodiment, a expandable component 41 (balloon or inflatable compartment) may be disposed at or proximal to the distal wire tip 29. The tip expandable component 41 may be the only expandable component on the guide wire 21 or the tip expandable component 41 may be in addition to the anchor expandable component 31. For instances whereby the tip expandable component 41 is the only expandable component on the guide wire, then the tip expandable component 41 may behave as an anchoring device in and of itself, such that it serves as a positioning device to prevent loss of wire position proximal to the lesion. Similarly, the anchor expandable component 31 may be the only expandable component on the guide wire 21. It should be appreciated that more than two expandable components (balloon or inflatable compartments) may be utilized with any of the combinations and embodiments discussed herein. It should be appreciated that the tip expandable component 41 at or proximal to the wire distal tip 29, as distinguished from the anchoring expandable component 31, will act as a trauma mitigating or trauma avoidance device or mechanism. For instance, when the guide wire distal tip 29 is positioned distal to the lesion then the tip expandable component 41 may be gently inflated so as not to rupture or perforate or damage the vessel 3. This will now allow the guide wire distal tip 29 to be less prone to injuring the vessel 3 as it is moved in a forward direction.

In an aspect of an embodiment of the present invention catheter device 10 and related method, the embodiment includes placing a small inflatable anchor expandable component 31 on a portion of the guide wire 21, which will be positioned just beyond the lesion 5 or stenosis. The anchor expandable component 31 will then be inflated just beyond the lesion 5 or stenosis to anchor the guide wire 21 so that it will be less likely for the guide wire 21 to be pulled backward across the lesion 5 (or stenosis). For instance, when a physician pushes a stent (not shown, for example, via a monorail stent catheter or an over-the-wire stent catheter) over the guide wire 21 forward against a resistant stenotic lesion 5 (or stenosis) the guide wire 21 will not back out or will be less likely to back out.

In an embodiment, the anchor expandable component 31 is inflated just distal to the lesion 5 (stenosis), wherein the lesion or stenosis itself would act as a further anchoring mechanism. Because the anchor expandable component 31 is inflated just beyond the lesion or stenosis the potentially injured endothelium could be covered by a drug stent. Specifically the expandable component 31 may be very short, e.g., less than about 4 mm (or sized/contoured as desired or required), so as to minimize endothelial contact surface area.

It should be appreciated that the anchor expandable component 31 may be a wide range of distances from the distal tip 29, whereby the distal extension 27 can be designed according to required or desired procedure/treatment and anatomy of the vasculature.

In an embodiment, a expandable component 41 may be disposed at or proximal to the distal wire tip 29, whereby the tip expandable component 41 (designed to prevent vessel trauma) may be the only expandable component on the guide wire 21 or the tip expandable component 41 may be in addition to the anchor expandable component 31. For instances whereby the tip expandable component 41 is the only expandable component on the guide wire, then the tip expandable component 41 may behave as an anchoring device in and of itself, such that it serves as a positioning device to prevent loss of wire position proximal to the lesion. As described above, if a guide backs out and the guide wire potentially backs out then the anchor expandable component 31 and/or tip expandable component 41 will maintain wire position distal to the lesion 5 or stenosis and the tip expandable component 41 will minimize vessel trauma if the to and fro motion or forward motion occurs with the distal guide wire tip 29.

Turning to FIG. 2, FIG. 2 illustrates a cross-section view II-II as shown in FIG. 1 of the catheter device 10. The catheter wire 21 comprises a lumen 22 disposed therein. The lumen 21 may be utilized for a variety of functions, for example, delivering inflation material to the anchor expandable component 31 and/or tip expandable component 41, as well as any other expandable component or inflation devices discussed throughout. The expandable components may be inflated by the lumen being connected to an inert gas, radiographic contrast, fluid or air delivery system at the operator end of the catheter, for example. It should be appreciated that a multi-lumen arrangement may be implemented as well. It should be appreciated that a multi-lumen may be implemented with 1) multiple tubes (or the like) or 2) with the approach of a single lumen (tube) having multiple inner compartments, channels, chambers, or lumens each constituting a separate lumen of the device, as well as any combination thereof. Each of the individual lumens or channels may have similar or distinct functions respective to one another. It should be appreciated that the guide wire can vary in diameter throughout its length thereby permitting a larger size lumen or multiple lumens in the larger diameter portion of the wire while maintaining a smaller wire tip capable of crossing tighter lesions.

Further, it should be appreciated that the anchor expandable component 31 and tip expandable component 41 may be any desired or required diameter according to desired or required procedure or particular vasculature. For instance, but not limited thereto, the diameter of the vasculature 3 may be about 3 mm and the diameter of the anchor expandable component may be about 2 mm while the diameter of the tip expandable component may be about one-half mm. These diameters are intended merely to be illustrative and should not be construed to be limiting in any manner. Further, in some approaches the diameter of the anchor expandable component and/or tip expandable component may be equal to or less than the diameter of the vasculature. In some approaches, the diameter of the anchor expandable component and/or tip expandable component may be greater than the diameter of the vasculature.

It should be appreciated that the expandable components 31, 41 discussed herein (as well as any additional expandable components or balloons referenced herein) may can take on all shapes along the entire continual geometric spectrum of manipulation of x, y and z planes of the guide wire to create a relatively conical, olive, ellipsoid, hemispherical, tubular, ring, cylindrical, multifaceted or spherical shape with changing of the long and short axes as well as the angle of curvature of the proximal and distal flared surfaces. Size of the expandable component or expandable component tip could also be manipulated by varying the compliance of the expandable component material and inflation pressure.

In an embodiment, the expandable components may include separate inflation devices corresponding to separate expandable components in x, y and z planes for the desired effect of shape manipulation. These separate expandable components could be covered by a covering expandable component material (e.g., outer membrane) or alternatively left bare or alternatively inflated to a pre-formed shape with only size manipulability.

Further advantages of expandable component inflation devices would be operator control of x, y and z planes of the expandable components thus enabling manipulation of shape as well as size in all planes to optimally and as atraumatically as possible intubate variably shaped and sized vasculature space. In some embodiments, the method of use of this invention may be similar to contemporary diagnostic and therapeutic catheters in some aspects, but with several important safety design features and options, and therapeutic advantages associated with the present invention. For example, regarding various embodiments of the present invention, from a safety standpoint the blunt, atraumatic (non-traumatic) expandable component or expandable component tip will allow traversal of all arterial vascular space much less traumatically and/or provide necessary anchoring. The blunt geometry of the present invention wire expandable components and related will enable contact with the vascular endoluminal wall that is atraumatic and mitigate damage or risk associated with unintentional guide wire withdrawal.

It should be appreciated that the expandable components 31, 41 (as well as any additional expandable components referenced herein) discussed herein may be single compartment expandable components, expandable components with multiple compartments, multiples expandable components or any inflation devices required for separate manipulation of x, y and z planes with a larger covering expandable component or expandable component like material or membrane covering the three x, y and z plane expandable components. This would enable more detailed and/or variable shape changes. Alternatively a "covering" expandable component (e.g., outer membrane) could be optional and/or alternatively a expandable component could have a pre-formed shape with only size of the expandable component being able to be controlled by the operator. Size of the expandable components could be a function of expandable component material compliance and inflation pressure.

Further, it should be appreciated that the shape of the expandable components may be may be semi-elliptical, as well as semi-spherical, hemispherical, semi-oval, partly rounded or partly olive.

It should be appreciated that the expandable components 31, 41 discussed herein (as well as any additional expandable components or balloons referenced herein) may have at least one the following shapes: olive, bulbous, rounded, spherical, hemispherical, conical, oval, tapered, beveled, chamfered, graduated and/or multi-faceted, or any combination thereof.

It should be appreciated that the expandable components 31, 41 discussed herein (as well as any additional expandable components or balloons referenced herein) may have at least one the following shapes: semi-elliptical, semi-spherical, hemispherical, semi-oval, partly rounded or partly olive, or any combination thereof.

It should be appreciated that the expandable components 31, 41 discussed herein (as well as any additional expandable components or balloons referenced herein) may have a pre-formed shape for inflation.

It should be appreciated that the expandable components 31, 41 discussed herein (as well as any additional expandable components or balloons referenced herein) may have at least one of the following shapes when at least partially inflated: cylindrical, tubular or ring-like.

It should be appreciated that the expandable components 31, 41 discussed herein (as well as any additional expandable components or balloons referenced herein) may be at least one of the following devices: expandable component, stent, sleeve, or any combination of such devices.

It should be appreciated that the expandable components 31, 41 discussed herein (as well as any additional expandable components or balloons referenced herein) may comprise a plurality of expandable components.

Next, referring to FIG. 3, FIG. 3 illustrates a schematic elevation view of an embodiment of the present invention catheter device 10 as similarly illustrated in FIG. 1, with the exception that apertures may be disposed on said anchor expandable component 31 and/or apertures may be disposed on said tip expandable component 41. The catheter guide 11 may include a catheter shaft 12 with a proximal portion 13 and distal portion 15 of the guide, interface device 17 and an orifice 18 defined by a guide catheter lumen 19. The catheter device 10 further includes a guide wire 21 that is inserted into a vasculature 3 (e.g., right coronary artery), such as an artery, vein or the like, as the catheter guide 11 sits at the ostium of the vasculature 3, at a proximal portion of the vasculature 3, or at a location of the vasculature as required or desired. The guide wire 21 includes a proximal portion 23 and distal portion 25 of the guide wire 21, and a distal tip 29, and an anchor expandable component 31 (or inflatable compartment) that may be disposed at or proximal to the beginning of the distal extension 27 of the guide wire 21, as well as any portion of the distal extension 27. The distal extension 27 may be any desired or required dimension such as about 100 com or more, about 10 cm or more, about 5 cm or more, 1 cm or more, less than about 1 cm, or less than 1 mm. The distance of the distal extension 27 may be any variable length according to the desired or required procedure/treatment on the subject or patient. In an embodiment, the distal extension 27 may be equal to zero thereby defining the location of the expandable component at or proximal to the distal tip 29. In an embodiment, a expandable component 41 (or inflatable compartment) may be disposed at or proximal to the distal wire tip 29. The tip expandable component 41 may be the only expandable component on the guide wire 21 or the tip expandable component 41 may be in addition to the anchor expandable component 31.

Still referring to FIG. 3, it should be appreciated that any element/part/portion or any combination of elements/parts/portions of catheter device 10, such as, but not limited thereto, the catheter shaft 12, proximal portion of guide 13, distal portion of guide 15, anchor expandable component 31 and/or tip expandable component 41 may have one or more apertures 21 disposed thereon to allow blood or other medium to flow there through. For example, if the anchor expandable component 31 and/or tip expandable component 41 or the like occludes or partially occludes any portion of the vasculature, such as a vessel and/or ostium, then blood flow would be allowed and/or directed to enter one or more apertures 33, 43 of the device 10 upstream (proximal) from the lesion 5 or distal tip 29 and exit downstream (distal) from the lesion 5 or distal tip 29.

While the non-limiting example of FIG. 3, illustrates apertures disposed on both the anchor expandable component 31 and/or tip expandable component 41 it should be appreciated that the apertures may be disposed on just one or the other.

It should be appreciated that any of the apertures 33, 43 discussed herein may have a variety of shapes, contours, sizes and dimensions as desired or required. Moreover, it should be appreciated that any of the apertures 21 discussed herein may be a variety of structures such as, but not limited thereto, recess, port, side hole, duct, perforation, duct, trough, bore, inlet/outlet, hole, channel, passage, slot, orifice or the alike. Further yet, it should be appreciated that any of the apertures 21 discussed herein may be disposed on any element/part/portion or any combination of elements/parts/portions of the catheter device 10 in a variety of locations circumferentially and axially.

The various embodiments of the present invention guide wire and expandable component(s) system and related method thereof as discussed throughout this document may be implemented with commercially available catheter devices, as well as the catheter devices disclosed in the following: 1) PCT Application No. PCT/US2005/037031, filed Oct. 14, 2005, entitled "Vasculature Catheter Device and Related Method of Using the Same," 2) U.S. Provisional Application Ser. No. 60/794,729, filed Apr. 25, 2006, entitled "Vascular Catheter Device and Related Method of Making and Using the Same," and 3) U.S. application Ser. No. 10/577,118, filed Apr. 26, 2006, entitled "Vascular Catheter Device and Related Method of Making and Using the Same," of which all of the above-referenced applications are hereby incorporated by reference herein in their entirety.

One skilled in the art can see that many other embodiments of the catheter device, and other details of construction and use constitute non-inventive variations of the novel and insightful conceptual means, system and technique which underlie the present invention.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:

1. A catheter device for a more effective and safer method of guide wire positioning and preventing vessel trauma for the practice of diagnostic vascular treatment and/or therapeutic vascular treatment of a subject's vasculature having a lesion, said device comprising:
   a guide catheter comprising a shaft having a proximal portion and a distal portion;
   said guide wire disposed in said guide catheter shaft having a proximal portion and a distal portion, said guide wire adapted to transfer beyond the lesion during at least a portion of the vascular treatment and/or therapeutic vascular treatment;
   a first expandable component disposed on said guide wire to be positioned distally beyond the lesion during at least a portion of the vascular treatment and/or therapeutic vascular treatment, said first expandable component being adapted to anchor said guide wire to mitigate and/or prevent loss of guide wire position during at least a portion of the vascular treatment and/or therapeutic vascular treatment to anchor:
   distal tip disposed or said distal portion of said guide wire:
   a second expandable component disposed at said distal tip of said guide wire, said second expandable component adapted to prevent and/or mitigate trauma to the vasculature during at least a portion of the vascular treatment and/or therapeutic vascular treatment; and wherein:
      segment of said distal portion of said guide wire that is located proximally before said distal tip provides a distal extension, and
      said distal extension or a portion of said distal extension separates said first expandable component and said second expandable component.

2. The device of claim 1, wherein said first expandable component has at least one the following shapes: olive, bulbous, rounded, spherical, hemispherical, conical, oval, tapered, beveled, chamfered, graduated and/or multi-faceted, or any combination thereof.

3. The device of claim 1, wherein said first expandable component has at least one the following shapes: semi-elliptical, semi-spherical, hemispherical, semi-oval, partly rounded or partly olive, or any combination thereof.

4. The device of claim 1, wherein said first expandable component has a pre-formed shape for inflation.

5. The device of claim 1, wherein said first expandable component has at least one the following shapes when at least partially inflated: cylindrical, tubular or ring-like.

6. The device of claim 1, wherein said first expandable component comprises a sleeve.

7. The device of claim 1, wherein said first expandable component comprises a plurality of expandable components.

8. The device of claim 1, wherein said first expandable component comprises at least one aperture disposed on wall of said first expandable component, wherein said at least one aperture being adapted to allow medium to flow there through.

9. The device of claim 1, wherein said distal tip having a blunt shape adapted to avoid or mitigate trauma with the vasculature.

10. The device of claim 1, wherein said second expandable component has at least one the following shapes: olive, bulbous, rounded, spherical, hemispherical, conical, oval, tapered, beveled, chamfered, graduated and/or multi-faceted, or any combination thereof.

11. The device of claim 1, wherein said second expandable component has at least one the following shapes: semi-elliptical, semi-spherical, hemispherical, semi-oval, partly rounded or partly olive, or any combination thereof.

12. The device of claim 1, wherein said second expandable component has a pre-formed shape for inflation.

13. The device of claim 1, wherein said second expandable component has at least one the following shapes when at least partially inflated: cylindrical, tubular or ring-like.

14. The device of claim 1, wherein said second expandable component comprises a sleeve.

15. The device of claim 1, wherein said second expandable component comprises a plurality of expandable components.

16. The device of claim 1, wherein said second expandable component comprises at least one aperture disposed on wall of said second expandable component, wherein said at least one aperture being adapted to allow medium to flow there through.

17. The device of claim 1, wherein the vascular diagnostic treatment comprises an invasive procedure in which the catheter device and related are passed into a peripheral vein or artery, through the blood vessels, and into the heart or other vasculature.

18. The device of claim 1, wherein the vascular diagnostic treatment comprises at least one of: coronary and peripheral vasculature angiography or coronary arteriography and angiography.

19. The device of claim 1, wherein the vascular therapeutic treatment comprises therapeutic cardiac catheterization including at least one of the following: percutaneous transluminal angioplasty (PTA) (alternatively, percutaneous transluminal coronary angioplasty (PTCA)), percutaneous coronary intervention (PCI), and percutaneous transluminal interventions (PTI).

20. A catheter method for a more effective and safer method of guide wire positioning and preventing of vessel trauma for diagnostic vascular treatment and/or therapeutic vascular treatment of a subject's vasculature having a lesion, said method comprising:

providing a guide catheter comprising a shaft having a proximal portion and a distal portion;

providing said guide wire disposed in said guide catheter shaft having a proximal portion and a distal portion, said guide wire having a distal tip;

transferring said guide wire beyond the lesion during at least a portion of the vascular treatment and/or therapeutic vascular treatment;

providing a first expandable component disposed on said guide wire, positioning said first expandable component distally beyond the lesion during at least a portion of the vascular treatment and/or therapeutic vascular treatment, and anchoring said guide wire using said first expandable component to mitigate and/or prevent loss of guide wire position during at least a portion of the vascular treatment and/or therapeutic vascular treatment to anchor;

providing a second expandable component disposed at said distal tip of said guide wire, and preventing and/or mitigating trauma to the vasculature using said second expandable component during at least a portion of the vascular treatment and/or therapeutic vascular treatment; an wherein:

a segment of said distal portion of said guide wire that is located proximally before said distal tip defines a distal extension, and said distal extension or a portion of said distal extension separates said first expandable component and said second expandable component.

* * * * *